(12) United States Patent
Kojima (10) Patent No.: US 11,051,683 B2
(45) Date of Patent: Jul. 6, 2021

(54) CONTROL DEVICE FOR IMAGING SYSTEM, IMAGING SYSTEM, AND METHOD FOR CONTROLLING IMAGING SYSTEM

(71) Applicant: OLYMPUS CORPORATION, Hachioji (JP)

(72) Inventor: Koji Kojima, Koganei (JP)

(73) Assignee: OLYMPUS CORPORATION, Tokyo (JP)

(*) Notice: Subject to any disclaimer, the term of this patent is extended or adjusted under 35 U.S.C. 154(b) by 532 days.

(21) Appl. No.: 15/953,967

(22) Filed: Apr. 16, 2018

(65) Prior Publication Data

US 2018/0228352 A1 Aug. 16, 2018

Related U.S. Application Data

(63) Continuation of application No. PCT/JP2016/079984, filed on Oct. 7, 2016.

(30) Foreign Application Priority Data

Oct. 27, 2015 (JP) ............................. JP2015-210942

(51) Int. Cl.
*A61B 5/00* (2006.01)
*A61B 1/06* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 9,414,739 B2 * 8/2016 Takekoshi .............. A61B 1/043
2015/0173595 A1 6/2015 Takekoshi et al.
2016/0302652 A1 * 10/2016 Morishita .............. A61B 1/043

FOREIGN PATENT DOCUMENTS

JP 2007-143624 A 6/2007
JP 2007-313171 A 12/2007
(Continued)

OTHER PUBLICATIONS

Mar. 28, 2017 Office Action issued in Japanese Patent Application No. 2017-508593.

(Continued)

*Primary Examiner* — Amelie R Davis
*Assistant Examiner* — Marjan Saboktakin
(74) *Attorney, Agent, or Firm* — Oliff PLC (57) ABSTRACT

A control device for an imaging system includes a video signal acquisition unit, a photometric unit, and a luminance control unit. The video signal acquisition unit is configured to acquire a video signal obtained by taking an image of fluorescence radiated from a subject under excitation by an excitation light that is emitted onto the subject. The photometric unit is configured to acquire brightness of the fluorescence based only on a color-specific video signal of one color corresponding to the fluorescence, the color-specific video signal being included in the video signal. The luminance control unit is configured to adjust luminance of a fluorescent image formed from the video signal, based on the brightness of the fluorescence acquired by the photometric unit.

3 Claims, 5 Drawing Sheets

(51) Int. Cl.
  *A61B 1/04*   (2006.01)
  *G02B 23/24*  (2006.01)
  *A61B 1/00*   (2006.01)
  *A61B 1/045*  (2006.01)

(52) U.S. Cl.
  CPC .............. *A61B 1/042* (2013.01); *A61B 1/043* (2013.01); *A61B 1/045* (2013.01); *A61B 1/0653* (2013.01); *A61B 1/0661* (2013.01); *A61B 5/0071* (2013.01); *A61B 5/0086* (2013.01); *G02B 23/2461* (2013.01)

(56) References Cited

FOREIGN PATENT DOCUMENTS

| | | |
|---|---|---|
| JP | 2010-005305 A | 1/2010 |
| WO | 2015/015839 A1 | 2/2015 |
| WO | 2015/115151 A1 | 8/2015 |

OTHER PUBLICATIONS

Dec. 27, 2016 International Search Report issued in International Patent Application No. PCT/JP2016/079984.

May 1, 2018 International Preliminary Report on Patentability issued in International Patent Application No. PCT/JP2016/079984.

* cited by examiner

| | Light source setting | Detection parameters | Luminance control | Display image |
|---|---|---|---|---|
| Normal light observation mode (WLI mode) | IR light source: off<br>R light source: on<br>G light source: on<br>B light source: on | R: 0.45<br>G: 0.45<br>B: 0.10 | Light source: adjusted<br>AGC: adjusted<br>Exposure: electronic shutter | Color image using R, G & B images |
| Infrared observation mode (IRI mode) (1st display mode) | IR light source: strong<br>R light source: off<br>G light source: on<br>B light source: on | R: 1.00<br>G: 0.00<br>B: 0.00 | IR light source: maximum<br>G & B light sources: adjusted<br>AGC: adjusted<br>Exposure: multi-exposure in plural fields | Cyan image based on R image |
| Infrared observation mode (IRI mode) (2nd display mode) | | R: 0.80<br>G: 0.20<br>B: 0.00 | | Cyan image based on R image superimposed on red image prepared based on G image |

CONTROL DEVICE FOR IMAGING SYSTEM, IMAGING SYSTEM, AND METHOD FOR CONTROLLING IMAGING SYSTEM

CROSS-REFERENCE TO RELATED APPLICATIONS

This application is a Continuation Application of PCT Application No. PCT/JP2016/079984, filed Oct. 7, 2016 and based upon and claiming the benefit of priority from prior Japanese Patent Application No. 2015-210942, filed Oct. 27, 2015, the entire contents of all of which are incorporated herein by reference.

BACKGROUND OF THE INVENTION

1. Field of the Invention

The present invention generally relates to a control device for an imaging system, the imaging system, and a method for controlling the imaging system.

2. Description of the Related Art

In general, when observing a subject with an endoscopic system, it has been known that the observation may be conducted not only under white light irradiation but also under irradiation of other types of light. It has been known, for example, that the irradiation of a certain excitation light may be adopted so as to observe the thereby generated fluorescence and obtain information that cannot be obtained from the observation under normal white light. Jpn. Pat. Appln. KOKAI Publication No. 2007-313171 discloses an endoscopic system configured to sequentially obtain a reflected light image and an autofluorescence image and superimpose these images, thereby offering the resultant image to the user. This publication also discloses the use of near-infrared light as the excitation light.

BRIEF SUMMARY OF THE INVENTION

According to an embodiment of the present invention, a control device for an image system includes a video signal acquisition unit configured to acquire a video signal obtained by taking an image of fluorescence radiated from a subject under excitation by an excitation light that is emitted onto the subject; a photometric unit configured to acquire brightness of the fluorescence based only on a color-specific video signal of one color corresponding to the fluorescence, the color-specific video signal being included in the video signal; and a luminance control unit configured to adjust luminance of a fluorescent image formed from the video signal, based on the brightness of the fluorescence acquired by the photometric unit.

According to an embodiment of the present invention, the imaging system includes the control device, a light source configured to emit the excitation light; and an imaging device configured to take an image of the fluorescence.

According to an embodiment of the present invention, a method for controlling an imaging system includes acquiring a video signal obtained by taking an image of fluorescence radiated from a subject under excitation by an excitation light emitted onto the subject; acquiring brightness of the fluorescence based only on a color-specific video signal of one color corresponding to the fluorescence, the color-specific video signal being included in the video signal; and adjusting luminance of a fluorescent image formed from the video signal, based on the brightness of the acquired fluorescence.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be explained with reference to the drawings. The present embodiment relates to an imaging system that acquires an image using a rigid medical scope and an imaging device. Specifically, the imaging system according to the present embodiment is provided with a function of taking an image of fluorescence emitted when irradiating a subject, which is an observation target, with excitation light.

Configuration of System

Figure 1:
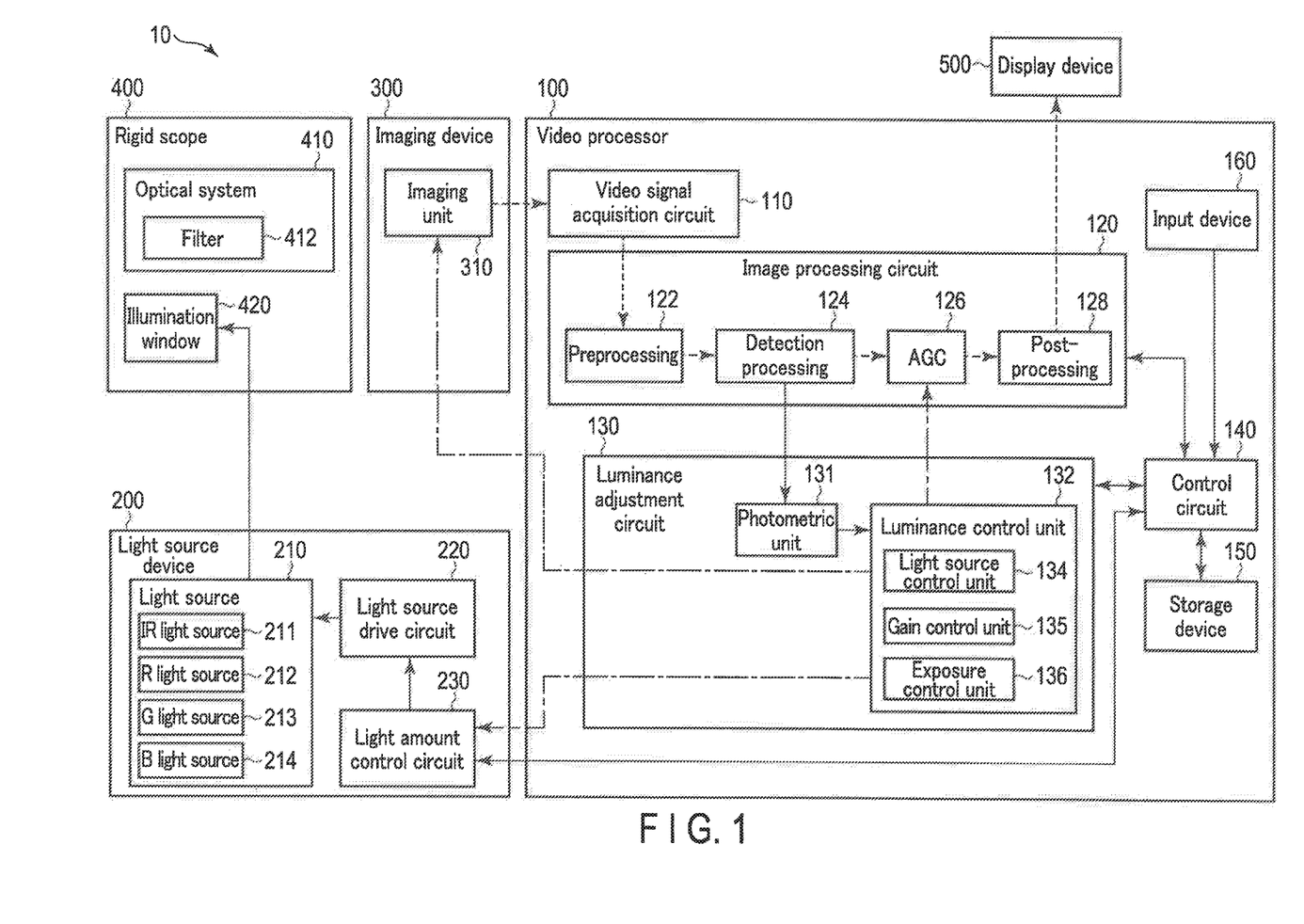
FIG. 1 is a schematic block diagram of an example configuration of an imaging system according to an embodiment of the present invention.

An example configuration of the imaging system 10 according to the present embodiment is illustrated in FIG. 1. As shown in this drawing, the imaging system 10 includes a video processor 100 that functions as a control device for the imaging system 10, a light source device 200, an imaging device 300, a rigid scope 400, and a display device 500. In FIG. 1, dashed arrows represent the flow of a video signal from the acquisition of the signal by the imaging device 300 up to the display on the display device 500. Dashed-dotted arrows represent the flow of a control signal for the luminance control that is to adjust the brightness of an image, which will be described later. Solid arrows represent the flows of signals other than the above-mentioned signals.

The rigid scope 400, which is a commonly used optical endoscope, is coupled to the imaging device 300. The imaging device 300 includes an imaging unit 310 having an image sensor and the like. The image sensor includes, for example, a CCD image sensor or a CMOS image sensor. According to the present embodiment, the imaging unit 310 adopts a 3-plane type. Alternatively, the imaging unit 310 may adopt a single-plane type. For an imaging unit of a single-plane type, an operation such as synchronization processing will be required. The imaging unit 310 uses the image sensor to generate a video signal for an image of the subject formed on the imaging surface of the image sensor.

The rigid scope 400 includes an optical system 410 and an illumination window 420. The optical system 410 forms an image of the subject on the imaging surface of the image sensor of the imaging device 300. The optical system 410 includes a filter 412 configured to block near-infrared light. The transmission characteristics of this filter 412 will be described later. The filter 412 may be arranged in front of the objective optical system, or as one of the optical elements within the relay lens. Alternatively, it may be arranged on the eye piece of the rigid scope 400. A similar filter may be arranged on the imaging unit 310 of the imaging device 300 instead of on the rigid scope 400. The illumination window 420 is a window through which the illumination light output from the light source device 200 is emitted. The illumination light emitted through the illumination window 420 illuminates the subject, the image of which is to be taken by the imaging unit 310.

The light source device 200 includes a light source 210, a light source drive circuit 220, and a light amount control circuit 230. The light source 210 has a plurality of light sources. In particular, the light source 210 includes an IR light source 211 that emits near-infrared light, an R light source 212 that emits red light, a G light source 213 that emits green light, and a B light source 214 that emits blue light. When the red light emitted from the R light source, the green light emitted from the G light source, and the blue light emitted from the B light source are combined, white light is prepared. These light sources may be constituted, for example, by various semiconductor light sources such as semiconductor laser light sources or light emitting diodes.

The light source drive circuit 220 drives the light sources included in the light source 210. The light amount control circuit 230 controls the operation of the light source drive circuit 220. Specifically, the light amount control circuit 230 controls the ON/OFF of the light source 210 and the intensity of the light emitted from each light source. The light emitted from the light source 210 is guided by a light guide fiber to the illumination window 420 of the rigid scope 400.

The amount of light guided to the illumination window 420 of the rigid scope 400 may be adjusted by the intensity of the light emitted by the light source 210, or may be adjusted with any other methods. For example, an aperture may be provided between the light source 210 and the light incident end of the light guide fiber to adjust the aperture ratio and thereby adjust the amount of light guided to the rigid scope 400. Furthermore, to change the output of the light source 210, the power supplied to the light source 210 may be adjusted by changing the current value, or by controlling a pulse width modulation (PWM).

The display device 500 is a commonly used display device such as a liquid crystal display. The display device 500 displays an image, based on a video signal that has been subjected to the image processing by an image processing circuit 120 of the video processor 100, which will be described later.

The video processor 100 includes a video signal acquisition circuit 110, an image processing circuit 120, a luminance adjustment circuit 130, a control circuit 140, a storage device 150, and an input device 160. The video signal acquisition circuit 110 acquires from the imaging device 300 a video signal generated by the imaging unit 310. The video signal acquisition circuit 110 conveys the acquired video signal to the image processing circuit 120. In this manner, the video signal acquisition circuit 110 serves as a video signal acquisition unit configured to acquire a video signal which is obtained by taking the image of the fluorescence.

The image processing circuit 120 executes various image processing operations onto the video signal acquired from the video signal acquisition circuit 110, and outputs the processed video signal to the display device 500. The processing executed by the image processing circuit 120 includes preprocessing 122, detection processing 124, automatic gain control (AGC) 126, and post-processing 128.

In the preprocessing 122, the video signal acquired from the video signal acquisition circuit 110 is subjected to color processing, noise reduction by filtering, gain adjustment, and the like.

In the detection processing 124, the video signal that has been subjected to the preprocessing 122 is multiplied by a detection parameter, which is a coefficient predetermined for each color. This detection parameter varies in accordance with the settings of the observation mode and the like. When the observation mode is a normal light observation (white light imaging; WLI) mode, the ratio of the video signals of the colors red (R), green (G), and blue (B) is set to R:G:B=0.45:0.45:0.10, as described later. For the infrared observation (infrared imaging; IRI) mode, the ratio of the video signals of these colors is set to R:G:B=1:0:0. If a background image is to be acquired in the infrared light observation mode, the ratio of the video signals of the colors is set to R:G:B=0.8:0.2:0.0. Furthermore, in the detection processing 124, predetermined gains may be applied. The video signals after the detection processing are conveyed to the luminance adjustment circuit 130, which will be described later.

In the AGC 126, in order to bring the intensity of the signal for each color that has been subjected to the detection processing 124 into a suitable range and thereby make the brightness of the image suitable, the gain for the video signal is adjusted. This gain adjustment is performed under the control of the luminance adjustment circuit 130.

In the post-processing 128, various image processing operations are performed, using the video signals that have been subjected to the AGC 126, to generate an image that is to be displayed on the display device 500. The video signals that have been subjected to the post-processing 128 are conveyed to the display device 500.

The luminance adjustment circuit 130 adjusts various operations of the imaging system 10 so that the image represented by the image signals that have been processed at the image processing circuit 120 will exhibit a suitable luminance. The luminance adjustment circuit 130 includes a photometric unit 131 and a luminance control unit 132. The photometric unit 131 acquires the video signals that have been subjected to the detection processing 124. The photometric unit 131 calculates the luminance of the image represented by the video signals based on the acquired video signals. The photometric unit 131 conveys the calculation result to the luminance control unit 132.

The luminance control unit 132 changes the settings based on the luminance information of the image acquired from the photometric unit 131. The luminance control unit 132 includes a light source control unit 134, a gain control unit 135, and an exposure control unit 136.

The light source control unit 134 adjusts the output of the light source 210 of the light source device 200 to make the brightness of the image suitable. The light source control unit 134 conveys the determined information regarding the output of the light source 210 to the light amount control circuit 230 of the light source device 200. The light amount control circuit 230 controls the operation of the light source 210 based on the information received from the control circuit 140, which will be described later, and the information of the output received from the light source control unit 134.

The gain control unit 135 determines the gain setting for the AGC 126, which is one of the parameters employed for the image processing performed at the image processing circuit 120, so as to make the luminance of the image suitable. The gain control unit 135 conveys the determined gain setting to the image processing circuit 120. The image processing circuit 120 performs the processing of the AGC 126 based on the gain setting acquired from the gain control unit 135.

The exposure control unit 136 determines the exposure setting of the imaging unit 310 of the imaging device 300 so as to make the brightness of the image suitable. The exposure control unit 136 conveys the determined exposure setting to the imaging unit 310. The imaging unit 310 performs an imaging operation based on the exposure setting acquired from the exposure control unit 136. The exposure time at the imaging unit 310, for example, may be determined based on this exposure setting.

The control circuit 140 controls the operations of the different components of the video processor 100. The control circuit 140 may be coupled to the image processing circuit 120 and the luminance adjustment circuit 130 to send commands for the operations of the image processing circuit 120 and the luminance adjustment circuit 130. The control circuit 140 is further coupled to the light amount control circuit 230 of the light source device 200 to send the necessary information to the light amount control circuit 230. The control circuit 140 may send to the light amount control circuit 230 the information, for example, as to whether the observation mode is the normal light observation mode or the infrared light observation mode, and whether the light source 210 should be on or off.

The storage device 150 includes, for example, a storage device such as a semiconductor memory or a hard disk. The storage device 150 is coupled to the control circuit 140. The storage device 150 may also be coupled to the image processing circuit 120 or the luminance adjustment circuit 130. The storage device 150 stores programs and setting values that are necessary for the operations of all the components.

The input device 160 may include an input device such as switches, a keyboard, or a touch panel. The control circuit 140 may receive commands from the user via the input device 160.

The image processing circuit 120, the luminance adjustment circuit 130, and the control circuit 140 include integrated circuits such as a central processing unit (CPU), an application specific integrated circuit (ASIC), or a field programmable gate array (FPGA). The image processing circuit 120, the luminance adjustment circuit 130 and the control circuit 140 may be each configured by a single integrated circuit, or may be configured by a combination of a plurality of integrated circuits. Alternatively, at least two of the image processing circuit 120, the luminance adjustment circuit 130, and the control circuit 140 may be configured by a single integrated circuit. These integrated circuits operate in accordance with the programs that are stored, for example, in the storage device 150 and the storage area of the integrated circuits. The light amount control circuit 230 of the light source device 200 also includes integrated circuits and the like.

System Operation

Figure 2:
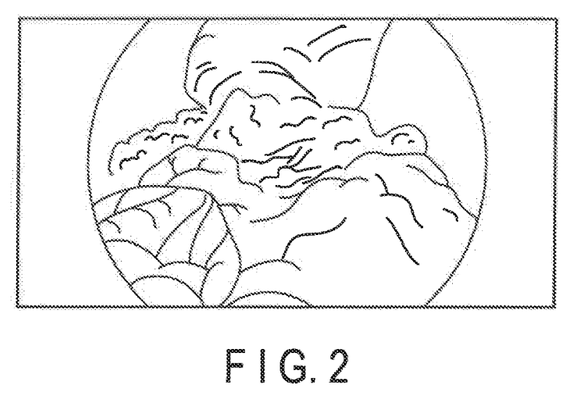
FIG. 2 is a schematic diagram of an example image obtained in a normal light observation mode.

The operation of the imaging system 10 according to the present embodiment will be explained below. The imaging system 10 has two observation modes; a normal light observation mode, in which an image of a subject is taken by irradiating the subject with white light and taking the image of the reflected light by the imaging device 300; and an infrared light observation mode, in which an image of the subject is taken by irradiating the subject with near-infrared excitation light and taking by the imaging device 300 the image of the infrared fluorescence generated by the excitation light. FIG. 2 schematically shows an image obtained in the normal light observation mode and displayed on the display device 500. In the normal light observation mode, the outer appearance of the subject can be observed.

Figure 3:
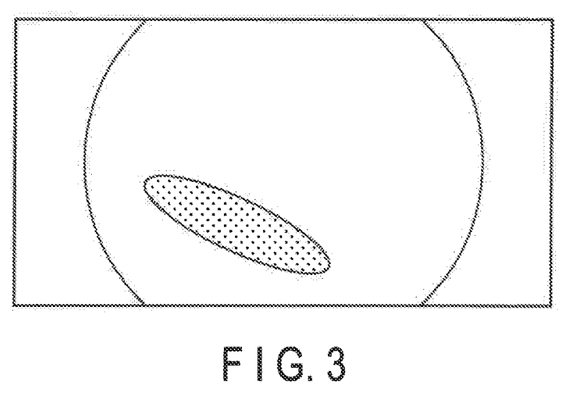
FIG. 3 is a schematic diagram of an example image obtained in an infrared light observation mode.
Figure 4:
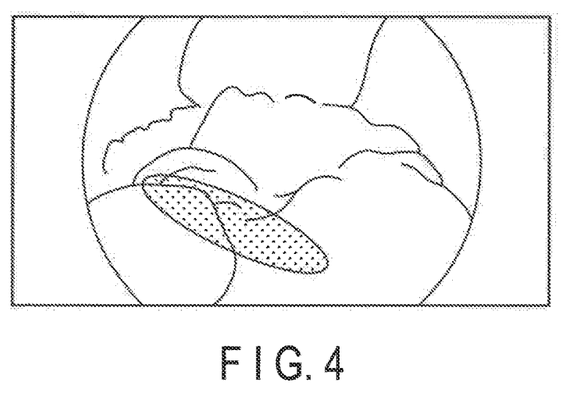
FIG. 4 is a schematic diagram of an example image obtained by superimposing a background image in the infrared light observation mode.

On the other hand, in the infrared light observation mode, specific objects such as a lesion and blood vessels in the deep portion of the mucosa can be observed. The infrared light observation mode includes a first display mode in which only the infrared fluorescence is displayed on the display device 500, and a second display mode in which a background image of a visible light region is superimposed onto the infrared fluorescence, and the superimposed image is displayed on the display device 500. FIG. 3 schematically shows an image obtained in the infrared light observation mode and displayed in the first display mode. The shaded portion in FIG. 3 schematically indicates where the fluorescence is observed. FIG. 4 schematically shows an image obtained in the infrared light observation mode and displayed in the second display mode. Although the resolution of the background image in the second display mode is not as high as in the normal light observation mode, the position of the fluorescent portion with reference to the background image can be acknowledged.

In general, a lesion is observed in the following manner: first, the observation is conducted in the normal light observation mode. For a suspected lesional area, the mode is switched from the normal light observation mode to the infrared light observation mode to examine whether or not it is a lesion. Thereafter, switching from the infrared light observation mode back to the normal light observation mode, a treatment such as incision of the lesion may be conducted with good visibility in the normal light observation mode.

Figure 5:
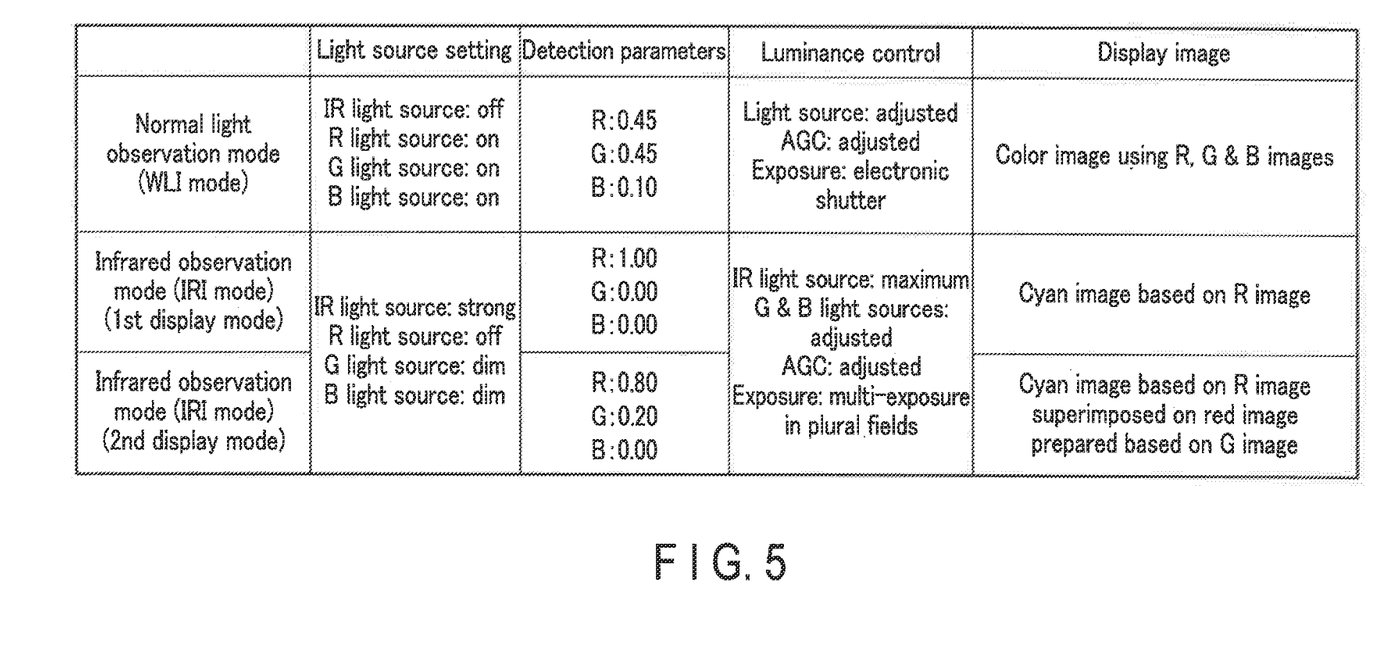
FIG. 5 is a list of examples of various settings for different observation modes.

In the imaging system 10, basic settings such as the output of the light source 210 and various parameters of the image processing circuit differ among different observation modes. Examples of the settings are shown in FIG. 5, where the settings for the light source 210, for the detection parameters of the detection processing 124, for the luminance controls conducted by the luminance control unit 132, and for the display image generation in the post-processing 128 are specified in accordance with the normal light observation mode, the infrared light observation mode (first display mode), and the infrared light observation mode (second display mode).

Figure 6:
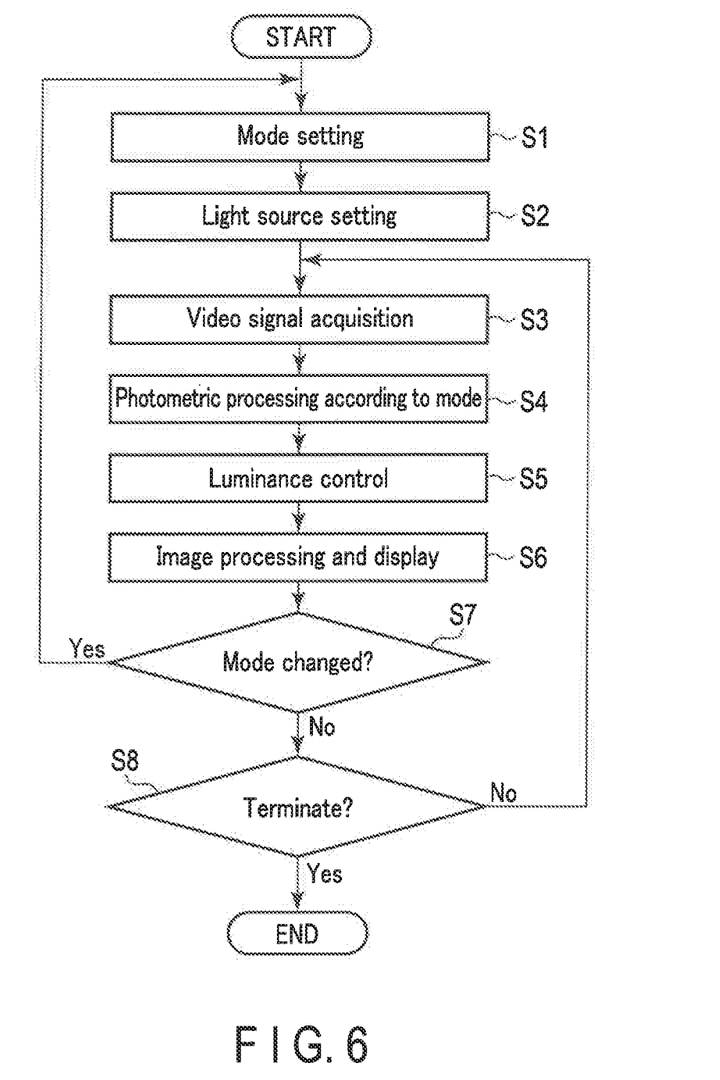
FIG. 6 is a flowchart showing an example operation of the imaging system.

The operation of the imaging system 10 according to the present embodiment will be explained with reference to the flowchart of FIG. 6.

In Step S1, the video processor 100 determines the settings for the observation modes and display modes. Specifically, the control circuit 140 acquires the information of the observation mode selected by the user on the input device 160. The control circuit 140 sets the setting values corresponding to the selected mode based on the acquired information.

In Step S2, the video processor 100 makes the settings of the light source 210. Specifically, the control circuit 140 outputs the information relating to the settings of the light source to the light amount control circuit 230 of the light source device 200, based on the mode settings. For example, the output of the IR light source 211 is turned off in the normal light observation mode, while the outputs of the R light source 212, the G light source 213, and the B light source 214 are turned on, as shown in FIG. 5. The outputs of these three light sources should be substantially equal to each other. Thus, the intensities of the emitted R light (red light), G light (green light), and B light (blue light) become substantially equal to each other, as a result of which the illumination light becomes white light.

Figure 7:
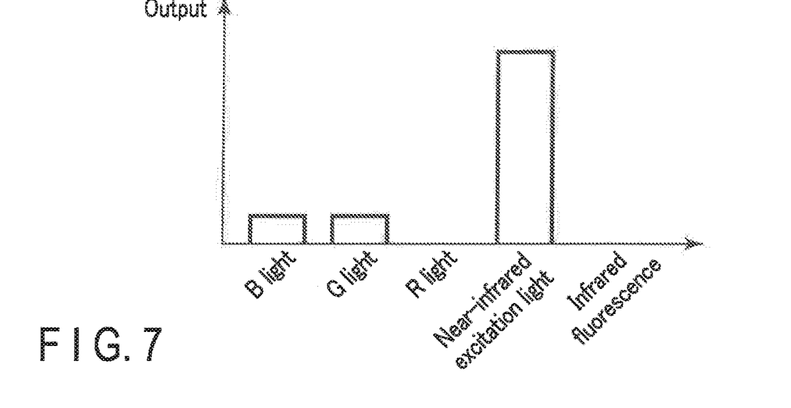
FIG. 7 is a chart schematically showing examples of the relationships between different light sources and their output intensities.

In the infrared light observation mode, the output of the IR light source 211 configured to emit near-infrared excitation light is increased, while the outputs of the G light source 213 and the B light source 214 are lowered. The output of the R light source 212 is turned off. The relationship between each light source and its output intensity is represented in FIG. 7.

White light is emitted onto the subject in the normal light observation mode. An image of the reflected light travelling through the optical system 410 of the rigid scope 400 is taken by the imaging unit 310 of the imaging device 300. In other words, the imaging device 300 creates video signals that include luminance information of different colors corresponding to the colors of the subject.

Figure 8:
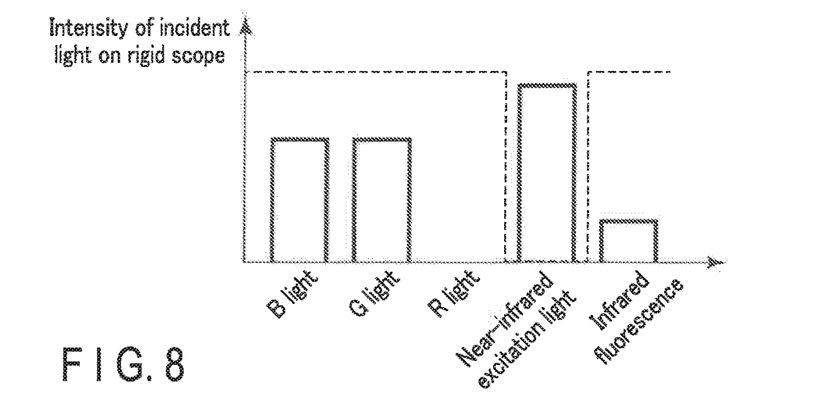
FIG. 8 is a chart schematically showing examples of the intensities of light of different frequencies incident on a rigid scope.

On the other hand, strong near-infrared light and dim B light and dim G light are emitted onto the subject in the infrared light observation mode. Upon this emission, the reflected light of the B light, G light, and IR light (near-infrared light) corresponding to the colors of the subject is incident on the optical system 410 of the rigid scope 400. In addition, the infrared fluorescence generated by the excitation with the IR light and having a longer wavelength than the near-infrared light is incident on the optical system 410 of the rigid scope 400. The intensity of each light having a certain wavelength that is incident on the rigid scope 400 is shown in FIG. 8. Of the illumination light, the intensity of the near-infrared excitation light is set higher than the intensity of the B light or G light, and therefore the reflected light of the near-infrared excitation light incident on the optical system 410 of the rigid scope 400 is stronger than the reflected light of the B light and G light. Although the near-infrared excitation light of the illumination light having an intensity higher than the intensities of the B light and G light, the intensity of the infrared fluorescence is lower than the intensities of the reflected light of the B light and G light. The transmission characteristics of the filter 412 included in the optical system 410 of the rigid scope is schematically shown with the dashed lines in FIG. 8. As can be seen from this chart, the filter 412 is configured to transmit the B light, G light, R light, and infrared light, while it is configured to block the near-infrared light that is the reflected light of the excitation light.

Figure 9:
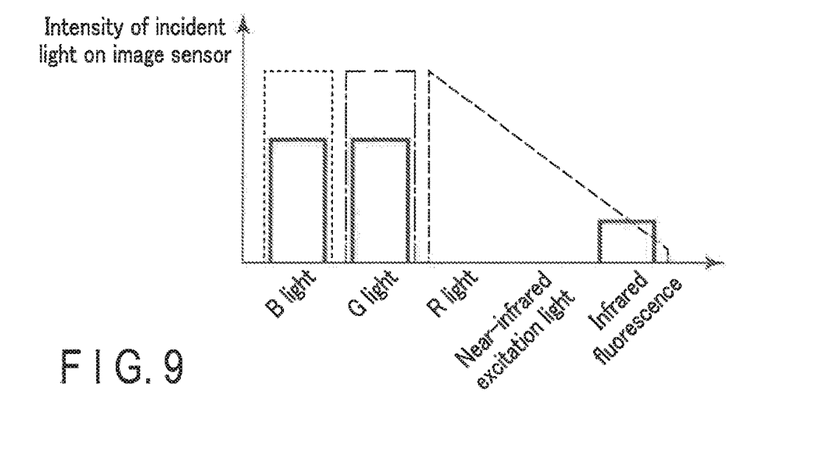
FIG. 9 is a chart schematically showing examples of the intensities of light of different frequencies incident on an image sensor.

The intensities of the light having different frequencies that pass through the filter 412 and are incident on the image sensor in the imaging unit 310 of the imaging device 300 are shown in FIG. 9. The near-infrared light, which is blocked by the filter 412, will not be incident on the image sensor, as can be seen from this chart. As a result, the B light and G light having a relatively high intensity and the infrared fluorescence having a relatively low intensity are incident on the image sensor.

The relationship between the wavelength and sensitivity of the image sensor that senses the blue light of the imaging unit 310 (B sensitivity element) is schematically indicated by the dotted line in FIG. 9. That is, the image of the B light is acquired by the B sensitivity element. The relationship between the wavelength and sensitivity of the image sensor that senses the green light of the imaging unit 310 (G sensitivity element) is schematically indicated by the dashed-dotted line. That is, the image of the G light is acquired by the G sensitivity element. The relationship between the wavelength and sensitivity of the image sensor that senses the red light of the imaging unit 310 (R sensitivity element) is schematically indicated by the dashed line. That is, the image of the infrared fluorescence is acquired by the R sensitivity element. It should be noted that the sensitivity of the R sensitivity element for the infrared light is not as high as the sensitivity for the R light. This means that the infrared fluorescence is not as easy to sense as the B light and G light. As described above, the imaging device 300 creates video signals that include luminance information of different colors corresponding to the colors of the subject and the amount of fluorescent substance.

In Step S3, the video processor 100 acquires a video signal. That is, the video signal acquisition circuit 110 acquires the video signals generated by the imaging unit 310 from the imaging unit 310 of the imaging device 300. These video signals are conveyed to the image processing circuit 120, where the video signals are subjected to the processing such as the color adjustment, noise reduction, and gain adjustment at the preprocessing 122. The video signals that have been subjected to the preprocessing 122 include an R image signal relating to the R light, a G image signal relating to the G light, and a B image signal relating the B light. The video signals for a specific color, such as R image signal, G image signal, and B image signal will be referred to as color-specific video signals. The preprocessing 122 will be followed by the detection processing 124.

As mentioned above, the detection parameters that are to be multiplied by the video signals of the different colors in the detection processing 124 differ from each other in accordance with the observation mode. The examples of the detection parameters in different modes are indicated in FIG. 5. A detection parameter for each color is multiplied in the detection processing 124, and the video signal to which a suitable gain is applied is conveyed to the photometric unit 131 of the luminance adjustment circuit 130.

In Step S4, the video processor 100 performs a photometric processing in accordance with the mode. In particular, the photometric unit 131 of the luminance adjustment circuit 130 receives the video signals that have been subjected to the detection processing from the image processing circuit 120, and performs the photometric processing based on these video signals. In the normal light observation mode, the video signals that include the luminance information of the R image signal, G image signal, and B image signal detected in the detection processing 124 are employed in the photometric processing. On the other hand, in the infrared light observation mode, the video signals that include the luminance information of the R image signal only detected by the detection processing 124, or in other words, the color-specific video signals, are employed in the photometric processing. In the second display mode of the infrared light observation mode, the detection parameters for red and green are 0.8 and 0.2, respectively. In the photometric processing, video signals including the luminance information of the R image signal and G image signal may be used, or the luminance information of the R image signal only may be used.

In Step S5, the video processor 100 performs luminance control based on the result of the photometric processing. That is, the luminance control unit 132 of the luminance adjustment circuit 130 adjusts the various parameters so as to make the luminance of the image represented by the video signals suitable. For example, the light source control unit 134 of the luminance control unit 132 adjusts the output of the light source 210 of the light source device 200. The gain control unit 135 of the luminance control unit 132 adjusts the gain for the AGC 126 performed by the image processing circuit 120. The exposure control unit 136 of the luminance control unit 132 adjusts the exposure at the imaging unit 310 of the imaging device 300.

In the normal light observation mode, the following setting may be made: the exposure of the imaging unit 310 is set so that an image will be created for every field. Furthermore, an image that is acquired by the imaging process is adjusted by using an electronic shutter to limit the exposure time within a field so that the image will not become unnecessarily bright. The gain for the AGC 126 is adjusted in accordance with the luminance. The output of the light source 210 is also adjusted in accordance with the luminance.

On the other hand, in the infrared light observation mode, the following settings may be made for the fluorescence having a low luminance: the output of the IR light source 211 of the light source 210 is set to the maximum value. When the background light is also to be acquired in the second display mode, the outputs of the G light source 213 and the B light source 214 of the light source 210 are adjusted in accordance with the brightness of the background. The gain for the AGC 126 is also adjusted in accordance with the luminance. The exposure of the imaging unit 310 is determined so that an image can be created for every one to six fields. The number of fields to form one image can be adjusted in accordance with the luminance. With the multi-exposures using a plurality of fields, an unnecessarily high gain does not have to be adopted for the image processing performed at the image processing circuit 120, and thereby the noise of the finally-displayed image can be reduced.

When attention is focused on the gains, the preprocessing 122 may use the application of at most a four-time larger gain, the detection processing 124 may use the application of at most an eight-time larger gain, and the AGC 126 may use the application of at most an eight-time larger gain. This means that at most a several hundred-time larger gain may be applied in total. With such a high gain, an observation can be sufficiently conducted even in the infrared light observation mode, in which the luminance is inadequate.

In Step S6, the video processor 100 performs image processing onto the video signals acquired by the imaging device 300 in accordance with the luminance control, and displays on the display device 500 an image that has been subjected to the image processing. That is, the image processing circuit 120 of the video processor 100 performs image processing including the AGC 126 under the control of the luminance control unit 132. The image processing circuit 120 outputs the image-processed video signals to the display device 500, and displays an image on the display device 500.

In the normal light observation mode, the image processing circuit 120 may combine the R image signal, G image signal, and B image signal, and creates a color image to be displayed on the display device 500. The image that is created in this step is similar to an image of the subject when observed with the naked eyes through the rigid scope 400.

In contrast, in the infrared light observation mode, an image that represents the intensity of the fluorescence is created to be displayed on the display device 500, based on the image acquired as an R image signal by the imaging unit 310. Here, for the video signal of the image to be displayed on the display device 500, the R image signal obtained by the imaging unit 310 is converted to a G image signal and a B image signal that correspond to the luminance of the R image signal. That is, the image to be displayed on the display device 500 includes a G image signal and B image signal that correspond to the luminance of the R image signal, or in other words, the intensity of the fluorescence emitted from the subject, which will result in a cyan image having a luminance corresponding to the intensity of the fluorescence. Because the sensitivity of the human eye (relative luminosity) has its peak in the band of green, the fluorescence that needs to call attention is displayed in a color close to green, instead of red, in the fluorescence observation. In this manner, the visibility of the fluorescence portion can be improved.

As a background image in the infrared light observation mode, an image representing the brightness of the background that is to be displayed on the display device 500 is created based on the G image signal obtained by the imaging unit 310. For the video signal of the image to be displayed on the display device 500, the G image signal obtained by the imaging unit 310 is converted to an R image signal corresponding to the luminance of the G image signal. That is, the image to be displayed on the display device 500 includes an R image signal that has the luminance of the G image signal acquired by the imaging unit 310, or in other words the luminance corresponding to the light-and-dark contrast of the subject, resulting in a red image that has a luminance corresponding to the contrast of the subject. Here, the fluorescence acquired as red is converted to cyan, and the background acquired as green is converted to red. This is because, in the observation of the inside of the body, the background usually looks red. The color of the image to be displayed is adjusted so as to reduce the discrepancy between the image displayed on the display device 500 in the normal light observation mode and the background image of the image displayed on the display device 500 in the infrared light observation mode, thereby mitigating the feeling of oddness when looking at the image.

In Step S7, the video processor 100 determines as to whether or not the observation mode has been changed. If the observation mode has been changed, the process returns to Step S1, and the operations in Steps S1 to S7 are repeated. If the observation mode has not been changed, the process proceeds to Step S8.

In Step S8, the video processor 100 determines whether or not the processing should be terminated. When it is determined not to be terminated, the process returns to Step S3, and the operations in Steps S3 to S8 are repeated. When it is determined to be terminated, the process is terminated. The operations in Steps S1 to S8 are repeated for every field at the timing of the field of the image taken by the imaging unit 310.

According to the present embodiment, in the infrared light observation mode, the photometric processing is performed using a video signal based on the R image signal only, or a video signal that is obtained by weighting the R image signal in the detection processing 124. Thus, the luminance control is performed in accordance with the R image signal that represents an image of the fluorescence having a low emission intensity. The imaging system 10 according to the present embodiment therefore realizes the acquisition of a fluorescent image having a suitable luminance. When a G image signal or B image signal is employed for the photometric processing, the luminance control tends to be conducted in a direction of lowering the luminance deriving from the R image signal in accordance with the high luminance deriving from the G image signal and B image signal, even if the luminance of the R image signal is low. In contrast, the invention according to the present embodiment avoids any inappropriate luminance control performed in the direction of lowering the luminance of the R image signal.

Modification Examples

Modification examples of the above embodiment will be explained below.

According to the above embodiment, the imaging system 10 that includes the normal light observation mode and infrared light observation mode as the observation modes has been discussed, but the present invention is not limited thereto. The above technique is equally applicable to an imaging system that includes the infrared light observation mode only.

According to the above embodiment, the near-infrared light is adopted as the excitation light, and the infrared light is adopted as the fluorescence, but the invention is not limited thereto. Light having any frequencies may be adopted as the excitation light and the fluorescence. The above technique may be applied to the autofluorescence observation, in which the fluorescence is obtained by exciting the fluorescent substances existing within the living body. In any case, the detection processing 124 detects a video signal corresponding to the fluorescence, and the photometric-processing is performed to acquire the brightness of the fluorescence based on the detected video signal.

According to the above embodiment, the imaging system 10 includes the rigid scope 400 and imaging device 300, but the present invention is not limited thereto. The above technique may be applied to a flexible scope that conveys an optical image, for example, with an optical fiber. The above technique is also applicable to an electronic endoscope having an image sensor at its tip. The electronic endoscope may be a flexible scope or a rigid scope. The above technique is not limited to an endoscope, but may be applied, for example, to a fluorescence microscope and other devices.

The light source 210 of the light source device 200 is described as including a plurality of laser light sources or light emitting diodes as light sources for different colors, but the invention is not limited thereto. For example, a semiconductor white light source may be adopted, in which a blue light source and a fluorescent substance are provided to emit a white light by combining the blue light emitted from this light source with the fluorescence emitted from the fluorescent substance when excited by the blue light as excitation light. As a light source, a lamp such as a xenon lamp or halogen lamp may be adopted. Furthermore, various other light sources that are not discussed in the above embodiment may be adopted as needed.

According to the above embodiment, all the light sources are arranged in a single light source device 200, but the invention is not limited thereto. For example, the near-infrared light source and the white light source (or any light sources that generate white light) may be arranged in different light source devices. Alternatively, at least one of the near-infrared light and the white light source or the like may be arranged integrally with the video processor 100.

According to the above embodiment, the image sensor included in the imaging unit 310 is defined as outputting video signals of three colors, red, green, and blue. The invention, however, is not limited thereto, and an imaging device that includes filters for complementary colors may be adopted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
    a light source device configured to emit a green light, a blue light, and a red light onto a subject in a normal light observation mode, and to emit the green light, the blue light, and excitation light based on near-infrared light onto the subject in an infrared light observation mode, wherein an output intensity of the excitation light is set higher than output intensities of the green light and the blue light;
    an imaging device configured to capture an image of return light of illumination light emitted from the light source device, the return light returning from the subject; and
    at least one processor configured to:
        acquire a video signal of the image captured by the imaging device;
        perform detection processing by determining a divided video signal for each color of red, green, and blue included in the image captured by the imaging device, and (i) multiplying each divided video signal by a respective first predetermined parameter set for each color based on the mode of the light source device, the predetermined parameters forming a first specific ratio of the normal light observation mode, and (ii) multiplying each of the divided video signals of the captured image for each color by a respective second predetermined parameter set for each color forming a second specific ratio, which is different from the first specific ratio, of the infrared light observation mode;
        calculate luminance based on a red image signal, a green image signal, and a blue image signal that have been subjected to the detection processing in the normal light observation mode, and calculate luminance based on a video signal that includes information of the red image signal only that has been subjected to the detection processing in the infrared light observation mode; and
        adjust an electronic shutter of the imaging device so as to form an image for each field based on the calculated luminance in the normal light observation mode, and set multi-exposure settings for the imaging device so as to form an image for a plurality of fields based on the calculated luminance in the infrared light observation mode.

2. The imaging system according to claim 1, wherein the processor is configured to set settings for gain adjustment of the video signal that has been subjected to the detection processing, based on the calculated luminance.

3. The imaging system according to claim 1, wherein the processor is configured to set settings for outputs of the light source device based on the calculated luminance.

* * * * *